United States Patent [19]

Appling et al.

[11] Patent Number: 5,267,979
[45] Date of Patent: Dec. 7, 1993

[54] PRESSURE RESPONSIVE VALVE CATHETER

[75] Inventors: William M. Appling, Hartford; Eamonn Hobbs, Queensbury; Daniel K. Recinella, Hadley; Arthur L. Zimmet, Centerport, all of N.Y.; Joseph J. Bookstein, La Jolla, Calif.

[73] Assignee: E-Z-Em, Inc., Westbury, N.Y.

[21] Appl. No.: 917,835

[22] Filed: Jul. 21, 1992

Related U.S. Application Data

[60] Division of Ser. No. 741,124, Aug. 7, 1991, which is a continuation-in-part of Ser. No. 583,466, Sep. 17, 1990, abandoned.

[51] Int. Cl.$^5$ ............................................. A61M 5/00
[52] U.S. Cl. .................................... 604/247; 604/249; 604/264; 137/537; 251/902
[58] Field of Search .................... 604/27, 31, 33, 50, 604/65, 107, 118, 121, 164-169, 245, 247, 249, 264, 282, 256, 99; 137/540, 537; 251/902

[56] References Cited

U.S. PATENT DOCUMENTS

| | | | |
|---|---|---|---|
| 960,080 | 5/1910 | Fay et al. ............................ | 251/902 |
| 2,996,077 | 8/1961 | Taggert ............................... | 137/537 |
| 3,503,400 | 3/1970 | Osthagen et al. .................. | 604/249 |
| 3,513,874 | 5/1970 | Welsh et al. ....................... | 251/902 |
| 3,841,308 | 10/1974 | Tate .................................... | 604/249 |
| 3,888,249 | 6/1975 | Spencer . | |
| 4,737,152 | 4/1988 | Alchas ................................ | 604/256 |
| 4,985,022 | 1/1991 | Fearnot et al. .................... | 604/282 |

Primary Examiner—C. Fred Rosenbaum
Assistant Examiner—Mark Bockelman
Attorney, Agent, or Firm—McAulay Fisher Nissen Goldberg & Kiel

[57] ABSTRACT

A catheter for introducing material into the vascular system is provided. The catheter includes an elongated catheter body having a side wall defining a catheter lumen. The catheter body has a proximal portion. Material can be introduced into the catheter lumen at its proximal portion. The catheter body has a distal portion. The distal portion has a single wall in an exit zone. At least one pressure responsive exit is formed in the side wall of the distal portion of the catheter body. The pressure responsive exit permits material to exit from the catheter lumen in response to a pressure over a first predetermined amount while preventing material from entering into the catheter lumen at a pressure less than a second pre-determined amount.

9 Claims, 6 Drawing Sheets

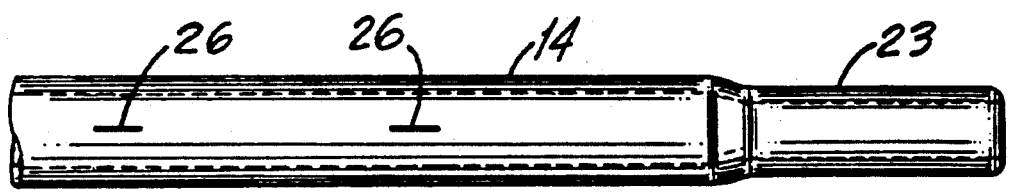
FIG. 12
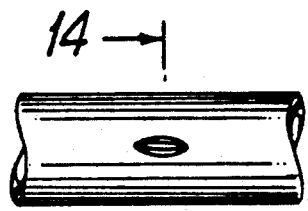
FIG. 13
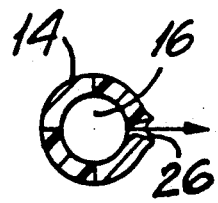
FIG. 14

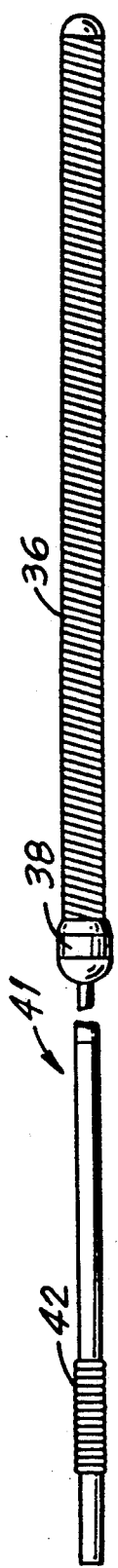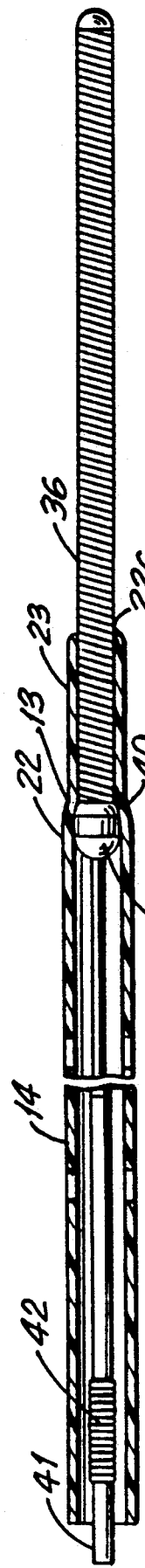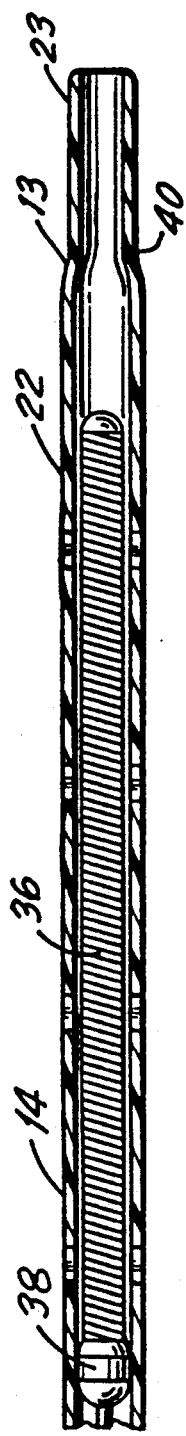

PRESSURE RESPONSIVE VALVE CATHETER

This application is a division of application Ser. No. 07/741,124 filed Aug. 7, 1991 pending, which is a continuation-in-part of Ser. No. 07/583,466 filed Sep. 17, 1990 now abandoned.

BACKGROUND OF THE INVENTION

The present invention relates to a catheter for use in the vascular system and, more particularly, to such a catheter which is formed with pressure responsive valves therein.

Catheters for delivery of fluids into the vascular system are known in the art. These catheters include a catheter lumen having a proximal end through which material is introduced into the catheter lumen and a distal end from which fluid exits from the catheter lumen. Some catheters are formed with a single distal end hole which serves both as a means of egress for the fluid and a passageway through which a guide wire can fit. In addition to an end hole some catheters are formed with multiple side holes. The provision of multiple side holes permits better mixing of fluid with blood, avoids a strong end hole jet, and permits a slightly higher flow rate. Some catheters with side holes have no end hole. Without an end hole the catheter cannot be used with a guide wire.

Catheters with multiple side holes may have problems with uniform fluid distribution. Additionally, multiple side holes create a problem where the guide wire may inadvertently exit from a side hole instead of from the end hole. Further, and especially where non-ionic contrast media is used, blood tends to clot at the side holes, which may cause delivery problems. Further, side holes are completely open and vulnerable to the ambient conditions surrounding them. Thus, when the catheter is in the vascular system it is possible, even at low pressure gradient, to get blood flow through the side holes into the catheter creating the possibility of clot formation in the side hole. Further, the use of multiple side holes can cause the outer wall of the catheter to be less smooth than desired resulting in an inadvertent gouging of the tissue. This is a bigger problent where the catheter is introduced at a site remote from the site where the fluid is to be delivered.

Catheters formed with slits, instead of holes, in the distal segment of the catheter are known in the art. The provision of slits in lieu of holes is intended to overcome some of the problems created by catheters with multiple side holes. A catheter formed with distal slits is disclosed in U.S. Pat. No. 3,888,249 issued to David L. Spencer on Jun. 10, 1975. The Spencer Patent disclosed a catheter for infusion of medication into an artery. The medication flows through the catheter lumen and exits into the artery through the distal slits which act as valves. The '249 catheter has a double wall in the area of the slits. It includes an inner wall with windows formed therein and an outer wall formed with slits therein. The slits overlie the windows. The modulus of elasticity of the outer wall is less than the modulus of elasticity of the inner wall and this difference in the elasticity of the two walls permit the slit/window combination to act as a valve. Another example of a catheter formed with slits rather than holes is disclosed in U.S. Pat. No. 4,973,319 issued to Gerald S. Melski on Nov. 27, 1990. The Melski Patent discloses a catheter for infusing fluids into a vein or artery. The fluids to be infused are therapeutic agents or nutrients. The Melski catheter, like the Spencer catheter, has a double wall in the area of the slits. The Melski catheter has an inner wall with apertures formed therein covered by an outer wall with slits formed therein. Melski discloses the use of a medical grade silicone rubber for both his inner and outer wall. However, Melski makes it clear that the inner wall should be made of a stiffer material than the outer wall in order for the two walls to work together to provide a one-way valve.

The catheters disclosed in the '249 and '319 patents may prove useful for delivering fluids at low pressure into the vasculature. Where a high pressure delivery is needed, however, the use of two walls to create the valve makes the valve incapable of withstanding repeated high pressure and/or high velocity injections. The walls may delaminate under these circumstances and the catheter would fail. An additional problem with the two walled construction described in these patents is that they have a step on the exterior surface of the catheter, where the inner tube fits into the outer tube, and this step provides a location for clot formation. An additional problem with the catheters disclosed in these patents is that they are relatively expensive to manufacture and fluid distribution problems may arise if the windows and slits are not properly aligned.

When catheters are used- for certain procedures it is desirable to insert the catheter at a site remote from the site where the fluid is to be injected. In such cases the catheter must be steered through the somewhat tortuous vasculature. In order to so do, the catheter itself must possess sufficient stiffness, torqueability, and pushability. In the alternative the catheter may be constructed for use with a guide wire, the guide wire providing the needed stiffness, torqueability, and pushability characteristics. Where a guide wire is to be used with a catheter, the catheter must be provided with an end hole. However, end holes can create problems when it is desired to deliver fluid with a uniform distribution along the length of the distal portion of the catheter.

Thrombolysis involves the dissolving of blood clots in the vascular system. There are a large number of people who need to have such blood clots dissolved. It has been proposed that the blood clots could be more efficiently lysed if the lytic agent were delivered to the clot at high velocity using a forceful injection. This would reduce the time needed to complete the procedure.

For optimal lysing, the lytic agent should be delivered at an even flow rate at the desired high pressure required for high velocity impact from exits provided along a predetermined length of catheter. Yet this high pressure/even flow rate function must be provided by a catheter which prevents back flow of blood into the catheter at ambient pressure.

It is an object of this invention to provide a catheter which provides the high pressure/even flow input function while meeting the other necessary objectives of such a catheter including preventing back flow of blood into the catheter at ambient pressure and providing a design which is capable of being steered through the vascular system.

It is a related purpose of this invention to provide this objective in a catheter which is relatively inexpensive to manufacture.

BRIEF DESCRIPTION

In one embodiment of the present invention a catheter for introducing material into the vascular system is provided. The catheter has an elongated catheter body. The elongated catheter body has an annular side wall which defines a catheter lumen. The catheter body has a proximal portion through which material, such as fibrinolytic agents, can be introduced into a catheter lumen. The catheter body also has a distal portion. The distal portion has a single wall in an exit zone. At least one pressure responsive exit is formed in the side wall of the exit zone. The pressure responsive exit permits material to exit from the catheter lumen while preventing material from entering into the catheter lumen.

BRIEF DESCRIPTION OF THE DRAWINGS

FIG. 12 is a side elevational view of another embodiment of the catheter of the present invention.

FIG. 13 is an enlargement of a portion of the distal end of the FIG. 12 catheter showing the slit in an open position.

FIG. 14 is a sectional view taken generally along line 14—14 of FIG. 13.

FIG. 15 is an elevational side view of an occluding wire intended for use with FIGS. 1-7, 12-14, and 18-20 embodiments.

FIG. 16 is a sectional view of the embodiment shown in FIG. 5 or 12 showing an occluding ball seated in the catheter distal taper and the end hole sealed.

FIG. 17 is analogous to FIG. 16 showing the ball unseated and the end hole open.

DESCRIPTION OF T-HE PREFERRED EMBODIMENT

Figure 1:
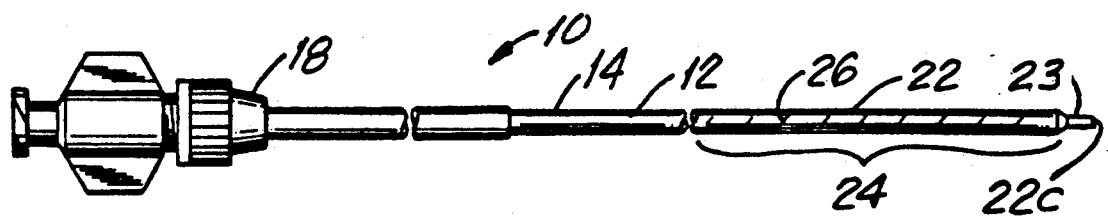
FIG. 1 is a side elevational view of one embodiment of the catheter of the present invention.
Figure 2:
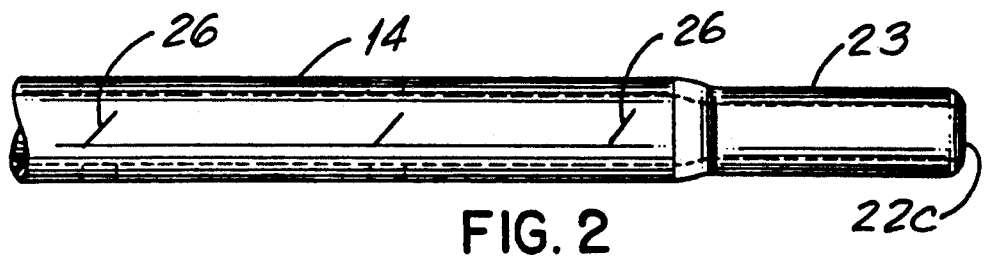
FIG. 2 is an enlargement of a portion of the distal end of the FIG. 1 catheter showing the slit in a closed position.
Figure 3:
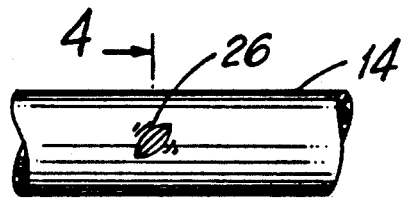
FIG. 3 is a view analogous to FIG. 2 showing the slit in an open position.
Figure 4:
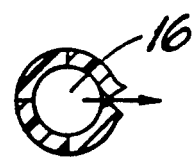
FIG. 4 is a sectional view taken generally along line 4—4 of FIG. 3 and indicating the direction of flow of material outwardly from the catheter slit.
Figure 5:
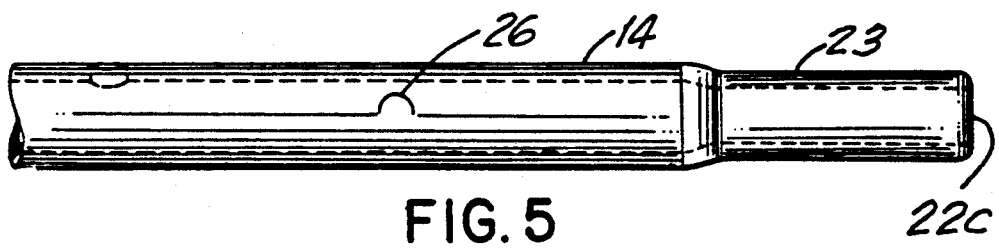
FIG. 5 is an enlarged view of the distal end of another embodiment of the catheter of the present invention showing a slit in the closed position.
Figure 6:
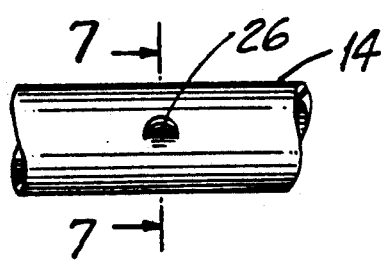
FIG. 6 is a view analogous to FIG. 5 showing the slit in the open position.
Figure 7:
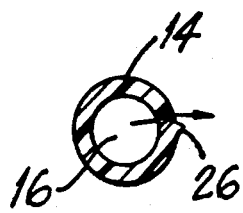
FIG. 7 is a sectional view taken generally along line 7—7 of FIG. 8 and indicating the direction of flow of material outwardly from the catheter slit.

Referring now to the drawings and more particularly to FIGS. 1-7 and 12-20, the reference numeral 10 denotes one embodiment of the catheter of the present invention. Catheter 10 is designed for delivering fluid into the vascular system. One intended use of catheter 10 is to deliver fibrinolytic agents to the site of blood clots to aid in lysing of the same. These fibrinolytic agents are delivered at low volumes and high velocities. For example, the volume is typically 0.2 ml to 0.5 ml (milliliters) over 5 to 200 milliseconds. For optimal lysing the fibrinolytic agent should be delivered with an even distribution so that the blood clots are dissolved in an accelerated and an efficient manner. Another intended use of catheter 10 is to deliver contrast media at a high, even flow rate for angiographic studies.

Catheter 10 has an elongated catheter body 12 with an annular side wall 14 defining a catheter lumen 16. The catheter body 12 has a proximal portion 18 with an opening (not shown) through which fluid is introduced into the catheter lumen. Catheter body 12 has a distal portion 22. The distal portion 22 includes an infusion length 24 with a plurality of slits 26 which serve as pressure responsive valves. In at least the areas of the infusion length 24, the catheter sidewall is a single wall.

As best shown in FIGS. 16 and 17, the distal portion 22 of catheter sidewall 14 includes a tapered zone 13. This taper 13 creates a seat 40 for an occluding ball 38 associated with an occluding wire 41. The inner diameter of the two portions of the catheter sidewall 14, proximal and distal of the taper 13, can vary dependent upon the intended use of catheter 10. In one embodiment of the invention, the catheter 10 has an inner diameter of about 0.047 inches and the end distal of the taper 13 is a straight portion 23 having a length of about 0.20 inches and an inner diameter of about 0.037 inches. The taper zone 13 has an angle of approximately 20 degrees and a length of about 0.02 inches.

Occluding wire 41 includes a distal coil spring 36 having an outer diameter of about 0.035 inches. Distal coil spring 36 protects the arterial wall from the catheter tip. Occluding ball 38 has a diameter of about 0.044 inches. When advanced in catheter 10, the occluding ball 38 seats in the taper 13 to seal the distal end hole 22c of catheter 10. By sealing end hole 22c fluid flow from the distal end hole 22c is prevented. Occluding wire 41 may be retracted to open end hole 22c. When the occluding ball 38 is seated and end hole 22c is sealed, all fluid flow is from the slits 26. When the occluding ball is not seated in the taper 13, both fluid and an associated guide wire (not shown) may exit from the end hole 22c.

Alternately, a shallow taper can extend along an end area of the catheter to reduce the catheter diameter to less than the diameter of the wire 41 so that a wire can be used to effect the sealing and unsealing of the end hole 22c.

Occluding wire 41 may be provided with a proximal platinum radiopaque marker 42 (see FIG. 15). When the occluding wire 41 is in place in the catheter, the marker 42 indicates the location of the most proximal slit. The occluding ball 38 helps locate the most distal slit. This aids in use of catheter 10 with fluoroscopy.

Figure 18:
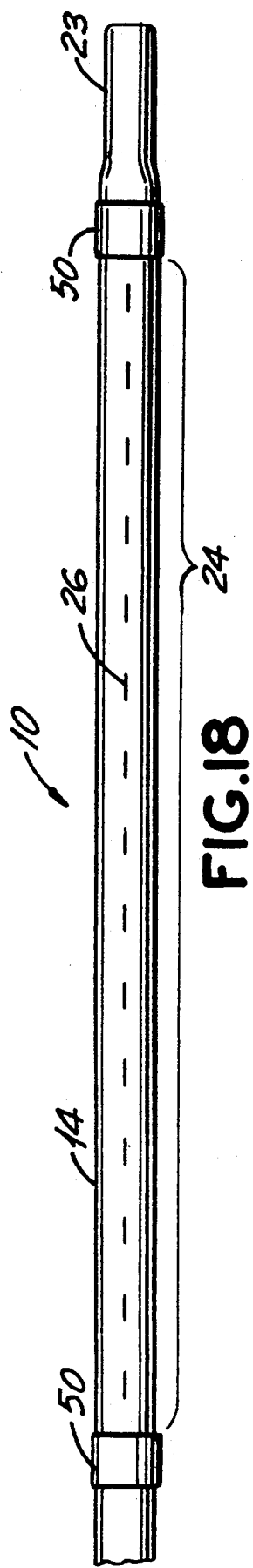
FIG. 18 is a view of he catheter in FIGS. 1-7, and 12-14 with radiopaque markers on the catheter shaft.

Another way to identify the infusion length and show slit locations can be done by placing radiopaque markers 50 on the catheter body 10 itself, as shown in FIG. 18. A marker 50 could be placed on the shaft, just proximal of the first proximal slit and just distal of the last distal slit. This would allow the catheter to be used with a conventional guide wire and yet still show slit locations.

Catheter 10 is formed of a relatively non-compliant material and in the preferred embodiment is formed of nylon. Material should have a flexural modulus in the range of $3 \times 10^4$ PSI to $1.0 \times 10^5$ PSI and be able to withstand internal pressures of at least 1,100 PSI. Slits 26 are integral with the catheter wall. The response of slits 26 to pressure is related to the flexural modulus of the slits and, the deflection of the slits is proportional to $WL^3/E$ where W equals load in pounds, L equals length in inches of the slits and E equals flexural modules of the material. The slits 26 are formed so that they will not deflect into the catheter lumen when the catheter is steered around a curve. This is necessary to allow catheter 10 to be advanced in the vasculature. The number of rows of slits and the area taken up by the slits in any radial plane, should be such that the tensile and compression strength of the catheter is not greatly compromised. This too allows the catheter to be advanced through the vasculature. The slits 26 should take up no more than about 20% of the side wall area in any radial plane and extend proximally along the shaft for a length of about 40% of the catheter length.

As catheter 10 is formed of a relatively non-compliant material, sidewall 14 does not swell when subjected to high internal pressures. Due to this, when catheter 10 is exposed to increased internal pressure, slits 26 flex open allowing fluid to flow from the interior lumen of the catheter therethrough. In each single embodiment of catheter 10 all of the slits 26 are of the same geometry and material and thus the load which will open each slit is the same. The slits will thus open almost simultaneously. When fluid is rapidly infused into the catheter, the pressure rise within the catheter lumen will be fast resulting in an approximate uniform load on all slits to result in a uniform flow of material out of all of the slits. Slits 26 open at a first predetermined internal pressure to allow material to exit from the catheter lumen. Slits 26 will not open, under ordinary circumstances, in response to external pressure. The slits 26 thus prevents back flow of material into the catheter 10. The slits 26 resist opening at low internal pressures and this allows flushing of the entire length of the catheter without problems of clot formation at the distal catheter end.

In a preferred embodiment the infusion length 24, encompassing the set of slits 26, is between 0.984 inches to 7.874 inches in length. As shown in FIGS. 1 through 4 and 12 through 14, slits 26 may be straight. The straight slits are equal in size and are equidistant from one another. The straight slits are longitudinally spaced from one another by 0.1 inches and are regularly spaced apart from one another by 90 degrees to thus provide four slits at each 0.1 inch interval along the length of the exit zone. The straight slits may be at an angle of about 45 degrees to a longitudinal side wall line. Alternatively they may be parallel to a longitudinal side wall line. The minimum opening pressure for the straight slits is one (1) psig. The straight slits will hold three (3) psig before allowing fluid to flow inwardly into the catheter. The slits allow good penetration and distribution of the fibrinolytic agent.

Alternatively, slits 26 may be semicircularly shaped. The semicircular slits each have a diameter of about 0.065 inches and are spaced longitudinally apart from one another by 0.1 inches and are radially spaced from one another by 90 degrees to provide one semicircular slit at 0.1 inch intervals along the infusion length 24. The semicircular slits have minimal opening pressure of 1 psig and will hold 3 psig before allowing fluids to flow inwardly into the catheter.

In the preferred embodiment, catheter 10 is a 5 French catheter. In one embodiment, the 5 French catheter is about 35.4 inches long. In another embodiment, the 5 French catheter is about 53.1 inches long.

The 35.4 inch catheter has in infusion length 24 of between 3.9 inches and 7.8 inches. The 53.1 inch catheter has an infusion length of between 3.9 inches and about 7.8 inches. Where straight slits are used in a catheter with a 3.9 inch infusion length 24, there are 80 slits, each having a length of 0.03 inches. Where the straight slits are used in a catheter with a 7.8 inch infusion length, there are 160 slits each having a length of 0.015 inches.

Figure 19:
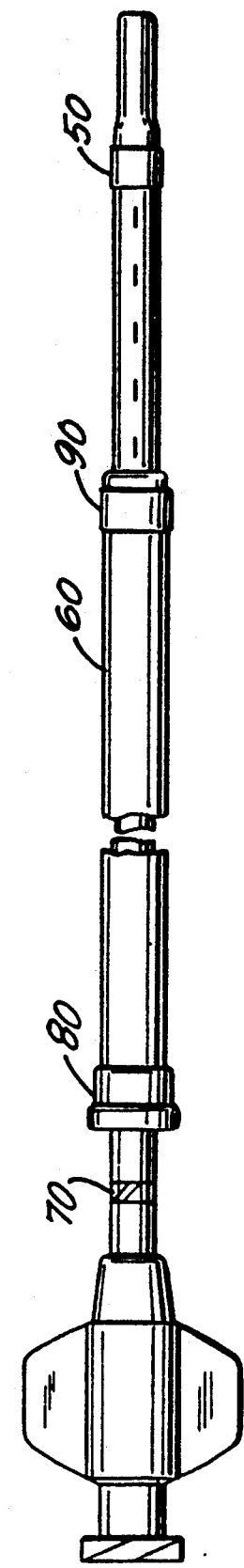
FIG. 19 is a view of variable infusion length catheter with the sleeve on the outside.

Alternatively, another design is shown in FIG. 19. This design shows a catheter such as those in FIGS. 1-7 and 12-14 having a sleeve 60 over the outer wall of the catheter. Sleeve 60 fits with a radial clearance of about one mil (0.001 inches). The sleeve 60 is made of a low friction polymer such as a polyolefin or fluoropolymer. Markings 70 on the catheter show advancement distance of the polymer sleeve down the body of the catheter 10.

Sleeve 60 is used to selectively cover the catheter slits 26 to prevent flow therethrough. The sleeve 60 provides high resistance against flow trying to exit from the covered slits. As fluid follows the path of least resistance it will exit from the non-covered slits. The use of sleeve 60 allows the user to adjust the desired infusion length by selectively covering some slits. The proximal end of sleeve 60 has a hub 80 for gripping. Radiopaque markers 50, 90 are provided at the distal end of the infusion zone and at the distal tip of the sleeve 60.

Figure 20:
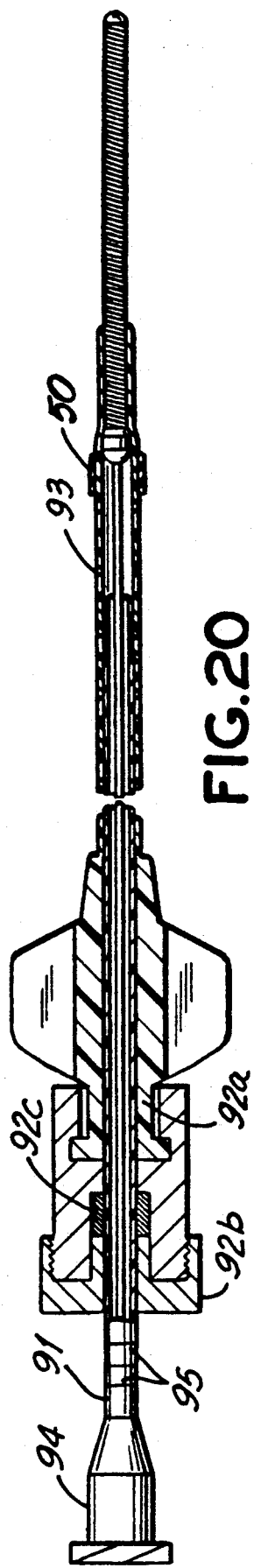
FIG. 20 is a view of a variable infusion length catheter with the sleeve in the catheter internal diameter.

FIG. 20 shows another method of providing the same variable infusion length. A sleeve 91 that fits into the inner diameter of the catheter is provided. A fitting 92 consisting of a body 92a, a cap 92b, and a grommet 92c is connected to the catheter hub. Sleeve 91 fits into the grommet and is advanced into the inner lumen of the catheter. Sleeve 91 is made of a polyolefin or fluoropolymer material, and has a distal tip radiopaque marker 93 and proximal hub 94. There are depth indicators 95 on sleeve 91. Advancing sleeve 91 into the catheter seals off slits thus giving variable infusion lengths. The slit infusion length is discernable using a radiopaque marker 93 on the sleeve 91 and a distal infusion length radiopaque marker 50 on the catheter. The occluding ball can also act as a distal infusion length marker.

Figure 8:
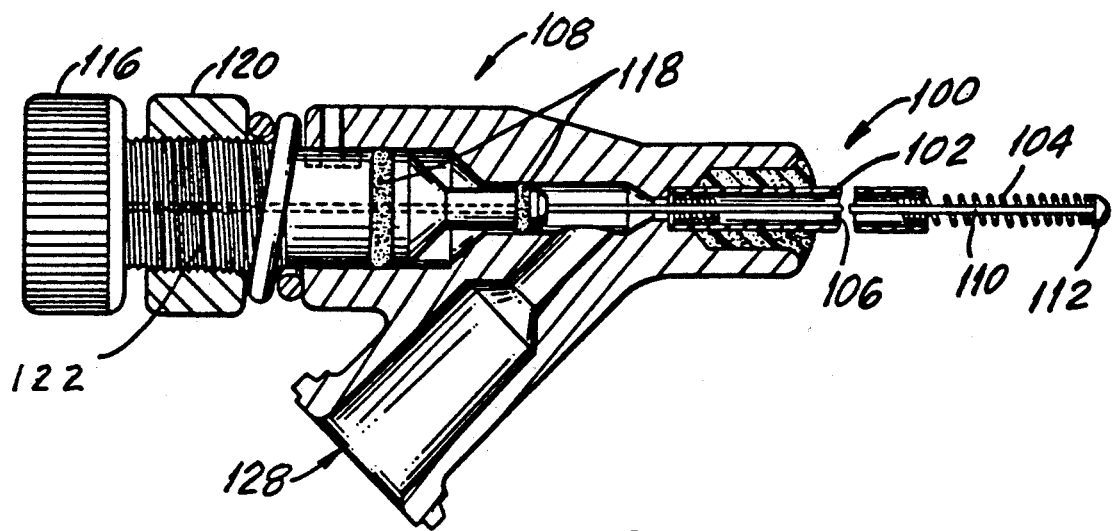
FIG. 8 is a sectional view of another embodiment of the catheter of the present invention showing a stainless steel coil defining a spiral slit and a polymer sleeve over the coil from the proximal hub to the open coil segment.
Figure 9:
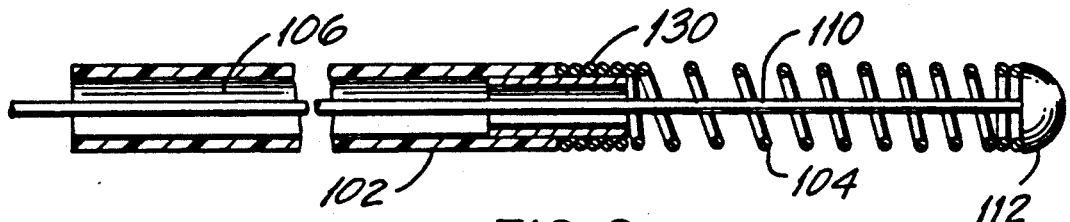
FIG. 9 is a sectional view of another embodiment of the catheter of the present invention showing the spiral slit with a partial polymer shaft.

Referring now to FIGS. 8 and 9, the reference numeral 100 denotes another embodiment of the catheter of the present invention. Catheter 100, like catheter 10, is designed for delivering fluid into the vascular system and more particularly is designed to deliver fibrinolytic agents, at high velocities, to the site of blood clots to aid in the accelerated and efficient lysing of the same.

Catheter 100 includes a polymer side wall 102 and an exposed distal coil 104 which together define a catheter lumen 106. A proximal hub 108 is provided. Polymer side wall 102 extends between proximal hub 108 and the exposed distal coil 104. A wire 110 connects the proximal hub 108 to the distal tip 112 of catheter 100.

The exposed distal coil 104 provides a single wall exit zone valve. The exposed distal coil 104 is normally held in a compressed state by a tension screw 116, an adjusting nut 120 and preloaded spring 122.

Exposed distal coil 104 has an outer diameter of about 0.03 inches and a length of about 0.2 inches to 0.79 inches. Connecting wire 110 serves to transfer force from the adjusting nut 120 and preload spring 122 to the distal coil 104. Adjusting nut 120 and spring 122 control the amount the distal coil 104 can open and by turning nut 120 the coils can be compressed. In a preferred embodiment the coil can open 0.001 to 0.003 inches, thus creating a slit that is open 360 degrees. Preload spring 122 also serves to keep the coil in the compressed state.

When an injection is commenced, fluid is injected into a side port 128 which communicates with catheter lumen 106. O-rings 118 are provided to seal the hub end to prevent proximal fluid flow. The fluid flows distally through the catheter lumen where the pressure produced by the flow forces the normally compressed coil to open so that fluid can exit from the coils. As shown in FIG. 9, the distal exposed coil may be attached to a piece of hypo-tubing 130 by bonding or soldering. The hypo-tubing 130 is fit into polymer side wall 102.

Figure 10:
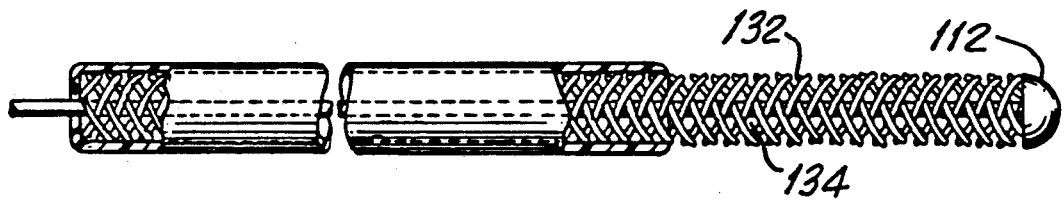
FIG. 10 is a sectional view of another embodiment of the catheter of the present invention showing a stainless steel braid and a polymer sleeve over the braid from the proximal hub to the open braid segment.
Figure 11:
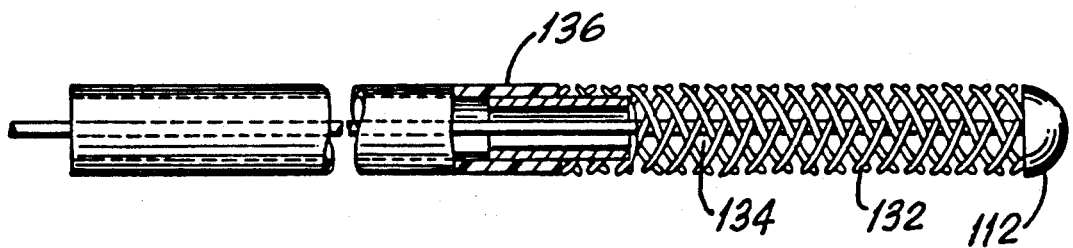
FIG. 11 is a sectional view of another embodiment of the catheter of the present invention showing a stainless steel braid and a partial polymer shaft.

As best shown in FIGS. 10 and 11, in lieu of a distal exposed coil a distal exposed braid 132 may be used with a catheter 100. Braid 132 is made of small diameter or flat wire and uses at least sixteen separate wires which are individually woven with a minimum of 32 picks or cross-overs per inch to provide a plurality of small openings 134 which act as valves. Both the braid and coil can be adjusted to achieve appropriate minimum opening pressures and to prevent backflow below a threshold pressure.

Figure 21:
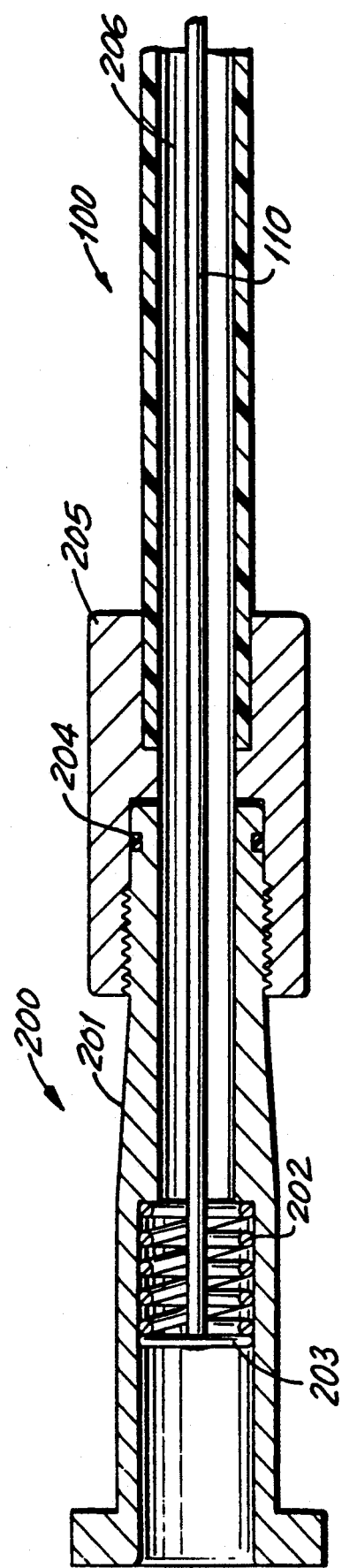
FIG. 21 is a cross-sectional view of an alternative hub design to be used with the catheters of FIGS. 8-11.

An alternative hub design for the FIGS. 8-11 embodiment is shown in FIG. 21. The hub 200 consists of a body 201, a compression spring 202, a platform 203, an o-ring 204, and a cap 205. The catheter 100 is attached to the cap. The wire 110 is attached to a platform. The platform 203 is a cross that abuts the compression spring 202. The hub body 201 screws into the cap 205. The O-ring 204 seals the inner wall of the cap 205. By screwing or unscrewing the body 201, a force is applied on the compression spring and transmitted down the wire 110 to the distal tip. Upon forceful injection, the flow hits the exposed coil or braid. The force of injection is transferred back to the platform 203 via wire 110. This causes the compression spring to be compressed which controls the amount the distal coil or braid can open.

This hub design has only one through lumen, making it easier to prime and assemble. Since the platform 203 is in the shape of a cross, the fluid can flow through its openings, through the compression spring 202 and to the catheter lumen 206.

The amount of coil or braid exposed in catheter 100 is dependent upon the use for which catheter is intended. The braid or coil provides catheter 100 with sufficient pushability, torqueability and stiffness to allow it to be steered through the vascular system without the need of a separate guide wire. Thus, there is no need to have an end hole associated with catheter 100. The outer diameter of the catheter cannot exceed 0.038 inches. This allows the catheter to behave similar to a guide wire in steerability and pushability. If needed, a standard balloon catheter could be advanced over the catheter 100.

What is claimed is:

1. A catheter for introducing material into the vascular system comprising:

an elongated catheter body having a sidewall defining a catheter lumen, said catheter body having a proximal portion with means through which material is introduced into the catheter lumen and a distal portion from which material can exit from said catheter lumen;

said catheter having an occluded distal end;

said distal portion being proximal of said distal end and capable of assuming an open position and a closed position, said distal portion when in its open position allowing fluid to exit from said catheter lumen, said distal portion when in its closed position preventing material from exiting from said catheter lumen, said distal portion moving from its closed position to its open position in response to fluid pressures equal to or greater than a predetermined internal fluid pressure, said distal portion serving as a pressure responsive exit to deliver material to the vascular system; and adjusting means for adjusting the predetermined internal fluid pressure necessary to move said distal portion from its closed position to its open position, said adjusting means including a pre-loaded spring and connecting means for connecting said pre-loaded spring to said distal end, said connecting means transmitting forces between said pre-loaded spring and said distal end said pre-loaded spring holding said distal portion in its closed position in the absence of said predetermined internal fluid pressure, said pre-loaded spring automatically causing said distal portion to return to its closed position in the absence of said predetermined internal fluid pressure;

said distal portion being formed such that it does not move from its closed position to its open position in response to a pressures equal to or less than a predetermined external fluid pressure.

2. The catheter of claim 1 wherein the predetermined external pressure is less than the predetermined internal pressure.

3. The catheter of claim 1 wherein said distal portion is a coil.

4. The catheter of claim 1 wherein said distal portion is a braid.

5. The catheter of claim 3 wherein said coil is made of stainless steel.

6. The catheter of claim 4 wherein said braid is made of stainless steel.

7. The catheter of claim 1 and further comprising a hub and a polymer sleeve, said hub positioned at the proximal end of the catheter, said sleeve positioned between said hub and said distal portion.

8. The catheter of claim 1 and further comprising a connecting wire, an adjusting nut, a tension screw, and a catheter hub, said connecting wire being connected to both the distal end of the catheter and the tension screw, the tension screw being inserted in the hub, the adjusting nut riding on the tension screw, and said pre-loaded spring being wrapped around the tension screw.

9. The catheter of claim 1 and further comprising a connecting wire, a platform, and a catheter hub, said connecting wire being connected to both the distal end of the catheter and the platform, said platform riding on said pre-loaded spring.

* * * * *